United States Patent [19]

Harandi

[11] Patent Number: 5,489,724
[45] Date of Patent: Feb. 6, 1996

[54] HIGH PRESSURE DROP ENDOTHERMIC PROCESS

[75] Inventor: Mohsen N. Harandi, Longhorne, Pa.

[73] Assignee: Mobil Oil Corporation, Fairfax, Va.

[21] Appl. No.: 354,708

[22] Filed: Dec. 13, 1994

[51] Int. Cl.$^6$ .......................... C07C 5/333; C07C 5/327; C10G 65/00
[52] U.S. Cl. .......................... 585/659; 585/310; 585/312; 585/317; 585/318; 585/319; 585/322; 585/324; 585/400; 585/407; 585/417; 585/444; 585/445; 585/654; 585/660; 585/661; 208/62; 208/63; 208/64; 208/65
[58] Field of Search .................... 585/310, 312, 585/317, 318, 319, 322, 324, 400, 407, 417, 444, 445, 654, 659, 660, 661; 208/62, 63, 64, 65

[56] References Cited

U.S. PATENT DOCUMENTS

| | | | |
|---|---|---|---|
| 4,069,135 | 1/1978 | Giuliani | 208/65 |
| 4,069,136 | 6/1978 | Peer et al. | 208/65 |
| 4,069,137 | 1/1978 | Greenwood | 208/65 |
| 4,935,566 | 6/1990 | Dessau et al. | 208/65 |
| 4,990,710 | 2/1991 | Dessau et al. | 585/277 |

Primary Examiner—E. Rollins Cross
Assistant Examiner—E. D. Irzinski
Attorney, Agent, or Firm—Alexander J. McKillop; Malcolm D. Keen; Richard D. Stone

[57] ABSTRACT

Aliphatic feeds are converted to olefins and/or aromatics in a multi pressure reactor system. A high pressure first stage reactor generates much or all of the hydrogen needed to reduce catalyst coking in lower pressure downstream reactors. High pressure operation protects catalyst stability in the first reactor, while produced hydrogen helps protect downstream catalyst. Low pressure downstream operation improves yields.

20 Claims, 1 Drawing Sheet

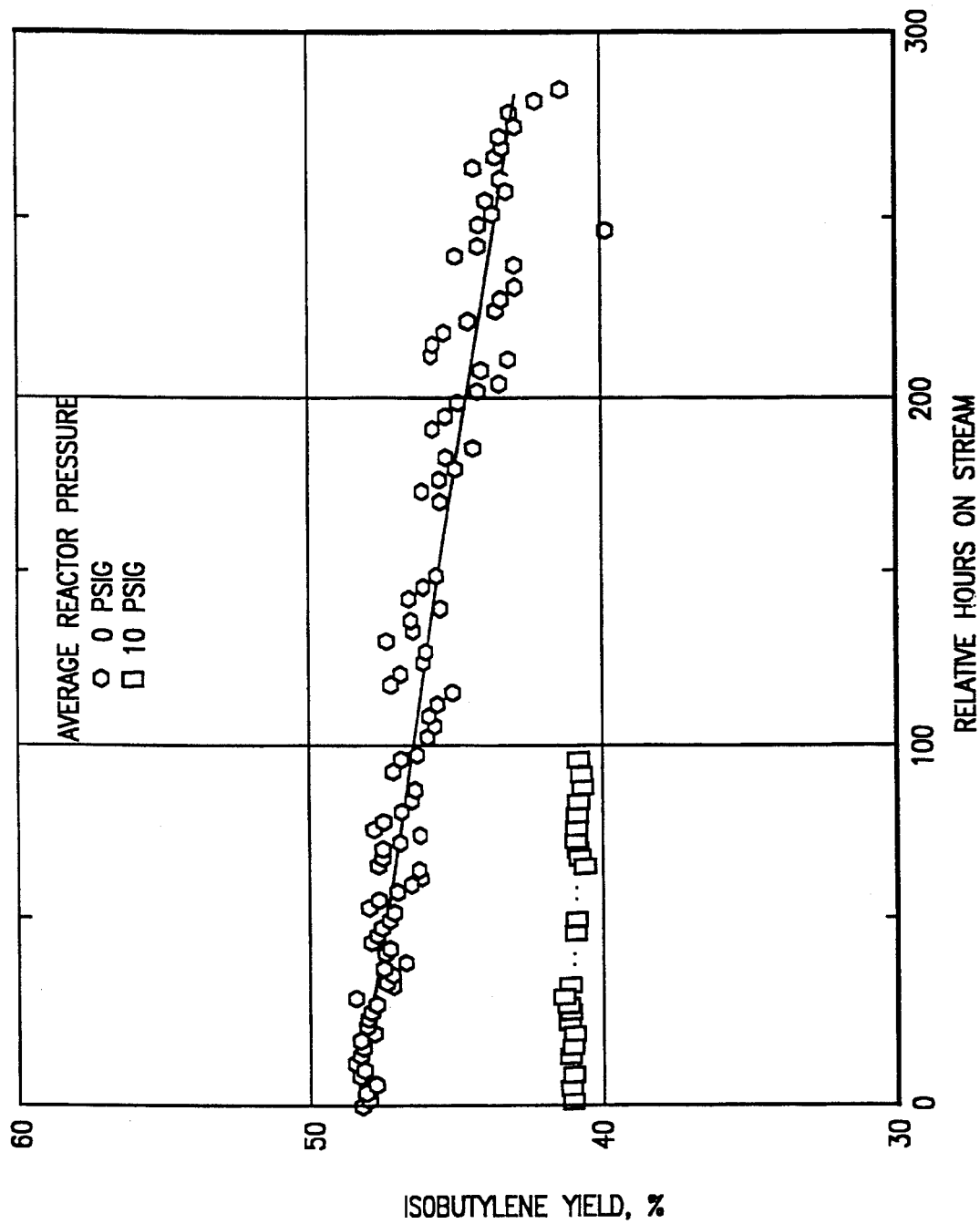

HIGH PRESSURE DROP ENDOTHERMIC PROCESS

FIELD OF THE INVENTION

The invention relates to paraffin dehydrogenation to produce olefins and dehydrocyclization to make aromatics.

BACKGROUND OF THE INVENTION

In the early days of the automobile, naphtha was recovered by simple fractionation from crude oil to produce gasoline. This was an adequate fuel for the low compression engines in use then, but as compression ratios increased there were demands for better fuel.

Thermal, and then catalytic, cracking produced gasoline of higher octane number. To meet demands for more octane refiners added lead compounds to gasoline, and/or installed alkylation units (using the light olefins generated by the cracking units) and catalytic reformers using platinum based catalyst.

The quality of the fuel increased, but so did the cost and complexity of the refinery. These complex refineries made a mix of clean fuels and fuels with relatively large amounts of sulfur and nitrogen or benzene.

Catalytic reforming produced a benzene rich gasoline of superior quality and low sulfur and nitrogen levels. Feed hydrotreating was required. Fortunately the reformer generally made enough hydrogen to supply the demands of its hydrotreater.

Alkylation produced excellent gasoline that was also a clean fuel. Alkylate was high in octane, and exceedingly low in sulfur, nitrogen and benzene because it was made from clean light hydrocarbons. Most of the feed to the alkylation unit was a byproduct of the catalytic cracking process. A clean fuel (alkylate) was made in parallel with large volumes of high octane catalytically cracked FCC naphtha, with a high sulfur and nitrogen content.

The demand for cleaner fuels has been difficult to cope with in many refineries. Refinery processes produce gasolines which are extraordinarily clean (alkylate and reformate) and which contain many impurities (FCC naphtha). Blending was a way to make moderately clean fuels, but could not be used to produce an adequate amount of reformulated gasoline.

Hydroprocessing of feed and product streams can help, but FCC naphtha will still have some sulfur and nitrogen in it. Such processing is expensive and requires hydrogen, which is not available in some refineries.

Refiners need more clean fuels, and in many instances even specific types of clean fuels, such as oxygenates. To make these materials olefins are usually needed, and there is no easy way to increase production of olefins. While processes and catalysts are known which can convert paraffins into olefins, these generally suffer from one or more of the following deficiencies:

Short catalyst life (if operated without $H_2$ addition).

Low conversion (if operated to maximize catalyst life).

High capital and operating expense (if operated with large amounts of hydrogen to extend catalyst life, or run at high conversion levels).

To summarize, most refineries do not have hydrogen to spare, and would like more olefins. Some refineries wish to run their dehydrocyclization units more efficiently, but without spending too much on recycle gas compression.

Some art on conversion of light paraffinic streams into olefins and/or aromatics will now be reviewed.

Some dehydrogenation catalysts, such as Pt-In-zeolite can be used without $H_2$ addition, but catalyst life is short unless large amounts of $H_2$ are added to the feed. Some of the extensive art on dehydrogenation technology will be reviewed.

U.S. Pat. No. 4,886,926 Dec. 12, 1989, Dessau, which is incorporated by reference, discloses making unsaturates from a paraffinic $C_2$–$C_5$ stream over catalyst of 0.01 to 30% Group VIII metal, preferably Pt, and non-acidic crystalline material containing 0.05 to 20% tin. The crystalline material is selected from the group of ZSM-5, ZSM-11, ZSM-12, ZSM-20, ZSM-23, ZSM-48, ZSM-50, MCM-22.

U.S. Pat. No. 4,935,566 Dessau, et al (Jun. 19, 1990), incorporated by reference, discloses dehydrocyclization and reforming paraffins over a non acidic platinum-tin containing crystalline micro porous material.

U.S. Pat. No. 5,192,728 Mar. 9, 1993, Dessau, which is incorporated by reference discloses a catalyst of a dehydrogenation metal and non-acidic crystalline material and tin.

U.S. Pat. No. 4,990,710, which is incorporated by reference, disclosed catalytic dehydrogenation using a low acidity dehydrogenation catalyst. Reactor "inlet $H_2$/feed ratios are 5 or less; even at reactor inlet ratios of zero (0), there will be a hydrogen partial pressure in the reactor because hydrogen is a bi-product of dehydrogenation." Col. 7 lines 16–29.

'710 summarizes the state of the art in dehydrogenation. The process can operate with no $H_2$ added, but adding, e.g., up to 5:1 $H_2$:HC molar basis makes the catalyst last longer.

Refiners wishing to catalytically convert paraffins into olefins or into aromatics are left with difficult choices. They can add lots of hydrogen to achieve a satisfactory catalyst life, and pay more for equipment to deal with the added vapor, which may include a hydrogen recycle gas system or regenerate catalyst frequently to remove the coke which rapidly forms. They also will see an adverse affect on equilibrium and hence conversion. Hydrogen addition to a hydrogen producing process suppresses to some extent hydrogen production. The alternative, operating with no hydrogen addition, results in drastically shortened catalyst life due to rapid coke buildup on the catalyst.

I discovered a way to have the best of both approaches. By operating my endothermic reactor(s), with an unusual approach to pressure drop, it was possible to obtain most of the catalyst life associated with high pressure operation while achieving most of the yield advantages associated with low pressure operation.

The first reactor or reaction zone runs at relatively high pressure, preferably with a modest amount of hydrogen present. Such high pressure operation gives relatively poor yields of hydrogen, but the catalyst exhibits great stability at such pressures. The hydrogen production from the first reactor provides a hydrogen rich atmosphere, which reduces coke formation in downstream reactors, even when the pressure is reduced to promote increased dehydrogenation or dehydrocyclization.

By operating this way it is possible to greatly reduce or perhaps even eliminate most or all of the capital and operating expenses associated with conventional hydrogen addition techniques. There is much less demand on the recycle gas compressor, even if one is used. It also increases the effective capacity of the heaters or heat exchangers used to preheat feed to the first reactor. A key benefit is reduction of the hydrogen partial pressure at the outlet of the last stage of the dehydrogenation reactor which allows maximum conversion of the paraffins.

BRIEF SUMMARY OF THE INVENTION

Accordingly, the present invention provides a process for removing a designated amount of hydrogen from an aliphatic hydrocarbon feed comprising at least some saturated hydrocarbons in the $C_2$ to $C_{12}$ range by passing said feed over a weight of catalyst having catalytic activity for removing hydrogen from aliphatic hydrocarbons comprising heating and vaporizing a high pressure liquid feed comprising said saturated hydrocarbons to produce a heated high pressure vapor stream having a designated temperature; charging to a first, high pressure, dehydrogenation reaction zone containing a portion of said catalyst said heated high pressure vapor and converting same in said high pressure dehydrogenation reaction zone to produce a first reaction zone effluent containing a limited amount of hydrogen; charging said first reaction zone effluent to a second reaction zone operating at a reduced pressure relative to said first reaction zone, and wherein the ratio of the absolute pressure in said second zone to said first zone is at least 1.35:1 and achieving in said second zone additional conversion of said first reaction zone effluent to produce said designated amount of hydrogen; and removing from said second reaction zone a reactor effluent stream of olefinic and/or aromatic product and produced hydrogen as a product of the process.

In another embodiment, the present invention provides a process for dehydrogenating paraffins in a single bed reactor to form olefins comprising heating and vaporizing a liquid feed comprising $C_2$ to $C_{12}$ saturated hydrocarbons and having a pressure of at least 25 psig to produce a heated vapor stream having a pressure of at least 25 psig; charging to a single reactor vessel containing one or more beds of a paraffin dehydrogenation catalyst said heated vapor having a pressure of at least 25 psig; depressuring and converting said vapor by passing said vapor through said catalyst in said reactor vessel, and wherein the absolute pressure of said vapor is reduced by at least 50% by passage through said catalyst; removing from said reactor vessel an effluent stream of olefinic and/or aromatic product and produced hydrogen as a product of the process.

In yet another embodiment, the present invention provides a process for dehydrocyclization of a feed containing $C_5$ to $C_{12}$ aliphatics in a multi reactor process comprising heating and vaporizing a liquid feed containing $C_5$ to $C_{12}$ aliphatics and having a pressure of at least 100 psig to produce a heated vapor stream having a pressure above 100 psig, charging heated vapor to a first dehydrocyclization reactor operating at dehydrocyclization conditions including a pressure above 100 psig and containing a dehydrocyclization catalyst and converting a limited amount of said feed to produce a first reactor effluent containing produced hydrogen charging said first reactor effluent to at least one downstream dehydrocyclization reactor operating at less than ½ the absolute pressure of said first reactor and containing a dehydrocyclization catalyst and converting in said downstream reactor additional amounts of said feed; and removing from said at least one downstream reactor a reactor effluent stream comprising aromatic products and produced hydrogen as a product of the process.

BRIEF DESCRIPTION OF THE DRAWING

The Figure is a plot of isobutylene yields over time at high and low pressure.

DETAILED DESCRIPTION OF PREFERRED EMBODIMENTS

Many parts of the endothermic conversion process, e.g., paraffin dehydrogenation or dehydrocyclization, can be conventional such as the catalyst, preheaters, reactors, etc. The unconventional part of the process is running the first reactor, at much higher pressure than terminal reactors. The process can be run in a single bed reactor, provided the inlet portion of a catalyst bed runs at a much higher pressure than the outlet portion of the catalyst bed. Conventional dehydrogenation and dehydrocyclization technology will be reviewed first.

PARAFFIN DEHYDROGENATION PROCESS

The paraffin dehydrogenation process of the present invention can use any catalyst heretofore used to convert paraffins into olefins. Typically these are low acidity materials with a hydrogenation/dehydrogenation component. Preferably the dehydrogenation catalyst is a microcrystalline material exhibiting little or no acid-catalyzed reactivity and containing from 0.01 to 10.0wt % Group VIII metal. Ideally the catalysts are non-acidic, as described by Davis and Venuto, J. CATAL. Vol. 15, p. 363 (1969), which is incorporated by reference.

Preferred zeolites have a silica/alumina mole ratio of at least 12, base exchanged to lower or essentially eliminate the base-exchangeable acidic content of the catalyst.

More details about suitable catalysts may be found in the following patents which are incorporated by reference.

U.S. Pat. No. 4,652,360 and its Division U.S. Pat. No. 4,699,708 disclose a base exchanged zeolite catalyst with shape selective metal function.

U.S. Pat. No. 4,849,567, Dessau et al, disclosed dehydrogenation over indium-containing crystalline microporous materials such as ZSM-5 and zeolite beta.

U.S. Pat. No. 4,886,926, Dessau taught making unsaturates from $C_2$–$C_5$ paraffins over Pt-Sn-ZSM-5, and related compositions. The support was ZSM-5, ZSM-11, ZSM-12, ZSM-20, ZSM-23, ZSM-48, ZSM-50, or MCM-22.

U.S. Pat. No. 5,192,728, Dessau, a division of U.S. Pat. No. 4,990,710, disclosed a non-acidic Pt/Sn-ZSM-5.

A good catalyst is a silica bound Pt/Sn-ZSM-5 containing 0.25 to 2.5 wt % Pt on an elemental metal basis and 0.5 to 5 wt % Sn, as disclosed in U.S. Pat. No. 5,192,728. Example 3 showed catalysts with 0.80 wt % Pt, 1.54 wt % Sn and 31 ppm Al. Example 10 showed use a 0.9% Pt/Sn-ZSM-5, though for naphtha reforming rather than production of olefins. The platinum was incorporated by ion-exchange of the calcined zeolites, and, it was reported, probably via exchange for sodium ions associated with internal silyloxy groups.

A suitable catalyst preparation technique is disclosed in U.S. Pat. No. 4,699,708 Oct. 13, 1987, which is incorporated by reference. This patent discloses making the catalyst with intrazeolitic Group VIII metal made by calcining at 200°–600° C. for 1–48 hours, then exchanging Group VIII metal, then thermally treating at 150°–550° C., followed by base exchange to produce a low acidity catalyst.

While the above catalysts are preferred, many other vendors supply dehydrogenation catalysts which convert paraffins to olefins, or that achieve other high temperature endothermic conversions, which may be used.

U.S. Pat. No. 5,093,540 teaches a catalyst for producing alpha olefins of an oxide of an alkali or alkaline earth metal optionally on an amorphous support.

U.S. Pat. No. 5,043,522 disclosed converting longer chain saturates to shorter chain olefins using H ZSM-5, 20X40 mesh. Other dehydrogenation catalyst, such as other low acidity zeolite based catalysts which are resistant to coking may also be used, but not necessarily with equivalent results.

DEHYDROCYCLIZATION/REFORMING

U.S. Pat. No. 4,935,566 Dessau, et al discloses dehydrocyclization and reforming paraffins over a non acidic platinum-tin containing crystalline micro porous material.

U.S. Pat. No. 4,982,028, Dessau discloses a VIII metal and a non-acidic crystalline indium material for dehydrocyclization.

SUBMOLAR HYDROGEN ADDITION

My process works well with $H_2$ addition, but does not require it. If any is added much less need be added than in conventional hydrogen producing processes. Modest amounts of $H_2$ addition, coupled with higher pressures in the inlet portions of the reactor work well together to reduce catalyst aging without burdening the plant with excess gas and without reducing conversion.

If hydrogen is added there should be less hydrogen than hydrocarbon, on a molar basis, at the catalyst bed inlet. Inlet $H_2$/hydrocarbon mole ratios should be below 0.5:1. Suitable $H_2$:HC mole ratios include 0.2:1 or less and preferably from about 0.02 to 0.1, more preferably from 0.03 to 0.08, and most preferably from 0.05 to 0.07.

My process can operate with trivial amounts of hydrogen addition. This makes it easy to operate with once through hydrogen addition.

As used herein, hydrogen to hydrocarbon mole ratios refer to moles of hydrogen at the inlet to the first reactor bed, and to moles of hydrocarbon feed to be dehydrogenated or reformed in the reactor. Methane which may be present in the hydrogen source e.g., reformer hydrogen, is ignored for purposes of calculating $H_2$:HC molar ratios.

DEHYDROGENATION PROCESS CONDITIONS

The temperature of the process can range from 900 to 1350, preferably from 1000 to 1150, and most preferably from 1000° to 1070° F. There can be great variation in average temperature needed to achieve a given conversion, due to differences in feed composition, catalyst activity, space velocity or conversion desired. Thus a low activity catalyst in unit with a high space velocity and high conversions may need an average bed temperature 100° to 150° F. higher than another unit with a more active catalyst, and more catalyst, which has lower conversion per pass.

The temperatures and space velocities employed can be conventional.

LHSV (liquid hourly space velocity) can range from about 0.1 to 100 and preferably is from 0.5 to 10.

The feed should contain a significant amount of $C_2$–$C_{12}$ aliphatics, e.g., a $C_2$–$C_3$ aliphatic stream, or a $C_5$–300° F. light naphtha fraction or some portion thereof. The feed may contain olefins and aromatics, but preferably is at least 60 mole % saturated. Pretreated or unpretreated ("straight run") naphtha may also be used.

An ideal charge stock is propane, butanes, pentanes or mixtures thereof.

Process conditions, and feedstock, are all somewhat related. High conversions are preferred.

For a process intended to produce olefins from paraffins, more than 20% of the feed paraffins should be converted to olefins, and preferably from 25 to 99% of the feed is converted.

PRESSURES

Inlet pressures may range from subatmospheric to 200 psig. Inlet pressures from about 1 to 100 psig give good results, provided there is enough pressure drop (from reactor to reactor or going through a reactor) that there is a significant increase in selectivity in the downstream bed. The absolute pressure drop is not as significant as the ratio of high to low pressure. Thus a 25 psi pressure drop may be ideal when the inlet pressure is 35 psig and the outlet pressure is 10 psig, representing a roughly 50% reduction in pressure. A 25 psi pressure drop would have little effect if the first reactor inlet pressure were 500 psig, and in fact normal pressure drop through a prior art reactor system would likely result in 25 psi dP from the first reactor inlet to the terminal reactor outlet.

Expressed in terms of ratios of pressure, the following guidelines may be given. The ratio of high to low pressures through the catalyst beds should be at least 1.35:1, and preferably is at least 1.5:1, and most preferably is 2:1. It may take some equipment modifications, but it is possible and beneficial to run with ratios of 3:1 or even higher.

Typically there is almost no significant energy consumption penalty associated with such a large pressure drop in the proposed process since the feed is normally liquid and has to be vaporized for the reaction anyhow. Typically the liquid feed stream is available at a higher pressure than the process requires. In conventional technology a significant portion of the pressure drop is taken across a valve while in this process such pressure drop is taken in the vapor phase as reactants flow through the catalyst bed.

Even when a relatively high pressure operation is required, which might be above the liquid feed supply pressure, the energy consumption associated with a high pressure first stage is less than might be thought. Most, and in some cases all, of the material charged to the reactors is pumped in as a liquid, at a pressure slightly above the desired inlet pressure. Heat, whether from heat exchange or from a fired heater, vaporizes the liquid. Pumping a liquid from a low pressure to a high pressure requires little energy, far less than compressing a much larger molar volume of recycle hydrogen case.

There is no yield penalty because the low pressure outlet of the process largely determines the yields. Catalyst life is sustained as the high pressure inlet reduces coking around the inlet, while the hydrogen produced in the high pressure side reduces coking in the low pressure side of the process.

Additional benefits flow from this process scheme. The high pressure drop available greatly simplifies the design of process units, there is no need to have an unusual low pressure drop heater. Distribution of fluids across reactor internals is greatly simplified when a large dP is available to make every orifice opening in a distributor active. The most efficient use of pressure drop is in a high pressure drop reactor design, which uses the energy in the flowing fluid continuously in getting through the bed. This allows use of smaller size catalyst particles to minimize diffusion limitations.

Simple tubular reactors, with the catalyst in the tubes, may be used. Such designs lend themselves to efficient heating, by putting some heat source around the tubes. There will be very little dead or stagnant regions in such a reactor, so the catalyst will be well used. This design allows use of tall tubes, minimizing the number of tubes needed, reducing the plot area required, and reducing the cost of the equipment.

DEHYDROCYCLIZATION/REFORMING

For a dehydrocyclization or reforming process, the conditions used are generally within the broad ranges heretofore found suitable for such processes. The most significant departures from conventional reforming and/or dehydrocyclization will be a much higher pressure drop getting through the reactors. Many refiners will also reduce or eliminate the amount of hydrogen rich recycle gas used, relying instead on much higher inlet pressures to reduce coking in the first reactor and in situ hydrogen production to reduce coking in terminal reactors.

The pressures used in my reforming process will generally be higher on the inlet side and lower on the side than are used conventionally. I do not require recycle of large amounts of hydrogen because much, or even all, of the hydrogen may be generated in situ. The reformer recycle gas compressor is the single largest capital and operating expense associated with many platinum reformers, but this can be significantly reduced in size, or eliminated, by using a high pressure rather than hydrogen recycle gas to reduce coking in the first reactor.

Temperatures may be conventional, and typically will be from 900 to 1100 at each reactor inlet, with interbed heaters used to reheat the reactor effluent prior to entry into a downstream reactor.

In a preferred embodiment, the reformer operates with no recycle gas compressor. A pump can economically supply the head needed to get liquid feed through pre-heaters and/or heat exchangers and reactors. The high pressure operation, perhaps coupled with some steps to reduce coke make such as reduced severity, protect the catalyst in the first reactor while hydrogen generated there will supply sufficient hydrogen to prevent excessive coking in the downstream reforming reactors.

The cost and constraints of catalytic reforming are transformed by using in situ hydrogen generation for much or all of the hydrogen needs of the plant. Using the prior art approach the capital and operating expense of the recycle gas compressor was frequently the limiting factor in plant design. The first reformers operated at 400–500 psig so that the cost of recycling large amounts of hydrogen would not be excessive. Refiners could go to lower pressure operation, 100 psig or less, only by using an expensive swing reactor system. Improvements in catalyst stability and activity, and moving bed reforming reactors, have since permitted much more latitude in selecting reformer pressure, but by no means eliminated the cost of the recycle gas system. In my process, there does not have to be a recycle gas compressor at all. This greatly simplifies the design and reduces the cost of the reformer, and allows the plant designer to achieve higher yields and more $H_2$ production, with the outlet pressure set as low as desired.

Where high pressure hydrogen is needed for other uses in the refiner, the plant may be run with a fairly high outlet pressure, e.g., 200 to 500 psig, to generate high pressure hydrogen, without involving the use of a compressor. Such high pressure operation will hurt yields, and will require much higher inlet pressures, but localized concerns may make such an option desirable.

REACTOR DESIGN

Any type of reactor design may be used, swing bed, moving bed, or fixed bed which permits a 20%–50%, or preferably even greater, pressure drop intermediate the first reactor inlet and the last reactor outlet.

The reactor may be a simple fixed bed, downflow reactor, with downstream reactors having the design disclosed in U.S. Pat. No. 4,973,778, which is incorporated by reference, where reactor tubes are heated directly by a fired heater. Use of tall narrow tubes, and/or using small particle size catalyst, can easily generate the high pressure drop needed for my process.

The preferred tube length for many commercial installations will be 25 feet or longer, with a catalyst particle size less than 3/8".

Multiple reactors may be used with fired heaters between reactors. Pressure drop may be usefully consumed in getting through high pressure drop heaters and/or upstream reactor beds or an expansion valve or power recovery turbine may be installed. The power recovery turbine would be somewhat different from power recovery turbines used in FCC regenerators in that the turbine could drive a generator and make electricity. In this way the process could become a net generator of energy in a refinery.

The reactors may be identical, or similar, or quite different. Thus two identical fixed bed reactors in series may be used, or a tubular reactor may be followed by a fixed bed reactor.

The feed to the first reactor can be heated by any conventional means, such as use of a fired heater or by indirect heat exchange with hot flue gas or process gas stream. Usually a fired heater will be used to supply at least some of the preheat.

EXAMPLES

Several tests were conducted in a small size test reactor using a low acidity Pt/Sn-ZSM-5 catalyst. The tests were run at 1030° F. at 3.5 weight hourly space velocity. The significant variables were time on stream and average reactor pressure.

The first run or first series of tests were run at atmospheric pressure (0 PSIG) for a total of about 300 hours on stream. These data points are presented as small circles on the Figure. Then additional tests were conducted with the same catalyst at 10 PSIG. These data points are represented by small rectangles in the Figure. The isobutylene yields are presented together in the Figure, showing that operation at low pressure gives much better olefin yields, but that the yields decline fairly rapidly. The yield decline is believed to be due to coke buildup on the catalyst. Operation at higher pressures is much more stable, although the yields of isobutylene are markedly reduced.

DISCUSSION

By operating with a high pressure inlet and low pressure outlet, yields and conversion can approach those of the low pressure portion of the plant while catalyst coking rates can be much lower than could have been predicted based on the outlet pressure and the inlet hydrogen partial pressure.

I claim:

1. A process for removing a designated amount of hydrogen from an aliphatic hydrocarbon feed comprising at least some saturated hydrocarbons in the $C_2$ to $C_2$ range by passing said feed over a weight of catalyst having catalytic activity for removing hydrogen from aliphatic hydrocarbons comprising:

a. heating and vaporizing a high pressure liquid feed comprising said saturated hydrocarbons to produce a heated high pressure vapor stream having a designated temperature;

b. charging to a first, high pressure, dehydrogenation reaction zone containing a portion of said catalyst said heated high pressure vapor and converting same in said high pressure dehydrogenation reaction zone to produce a first reaction zone effluent containing a limited amount of hydrogen;

c. charging said first reaction zone effluent to a second reaction zone operating at a reduced pressure relative to said first reaction zone, and wherein the ratio of the absolute pressure in said second zone to said first zone is at least 1.35:1 and achieving in said second zone additional conversion of said first reaction zone effluent to produce said designated amount of hydrogen; and d. removing from said second reaction zone a reactor effluent stream of olefinic and/or aromatic product and produced hydrogen as a product of the process.

2. The process of claim 1 wherein said catalyst is a micro-crystalline material exhibiting substantially no acid-catalyzed reactivity and having from 0.01 to 10.0 wt % Group VIII metal, on an elemental metal basis.

3. The process of claim 1 wherein no hydrogen is recycled from reactor effluent to mix with said aliphatic feed.

4. The process of claim 1 wherein the ratio of pressure in said second reactor to pressure in said first reactor is at least 1.5:1.

5. The process of claim 1 wherein said catalyst is a non-acidic Pt-Sn-ZSM-5.

6. The process of claim 1 wherein said feed comprises paraffins and 20–60% of said paraffins are converted to olefins.

7. The process of claim 6 wherein said feed is at least 50 wt % $C_2$–$C_5$ paraffins.

8. The process of claim 1 wherein said feed comprises $C_5$+ hydrocarbons which are converted to aromatics.

9. The process of claim 1 wherein said first reaction zone operates at a temperature of 900° to 1100° F. and pressure of 50 to 250 psig and said second reaction zone has an outlet pressure less than ½ of said first reaction zone.

10. A process for dehydrogenating paraffins in a single bed reactor to form olefins comprising:

a. heating and vaporizing a liquid feed comprising $C_2$ to $C_2$ saturated hydrocarbons and having a pressure of at least 25 psig to produce a heated vapor stream having a pressure of at least 25 psig;

b. charging to a single reactor vessel containing one or more beds of a paraffin dehydrogenation catalyst said heated vapor having a pressure of at least 25 psig;

c. depressuring and converting said vapor by passing said vapor through said catalyst in said reactor vessel, and wherein the absolute pressure of said vapor is reduced by at least 50 % by passage through said catalyst;

d. removing from said reactor vessel an effluent stream of olefinic and/or aromatic product and produced hydrogen as a product of the process.

11. The process of claim 10 wherein said catalyst is disposed in a plurality of vertical tubular reactors operating in parallel and having a length of at least 25 feet.

12. The process of claim 10 wherein said heated vapor charged to said reactor has a pressure of at least 100 psig,..

13. The process of claim 10 wherein no hydrogen is recycled from reactor effluent to mix with said aliphatic feed.

14. The process of claim 10 wherein said catalyst is a non-acidic Pt-Sn-ZSM-5.

15. The process of claim 10 wherein 20–60% of said paraffins are converted to olefins.

16. The process of claim 15 wherein said feed is at least 50 wt % $C_2$–$C_5$ paraffins.

17. The process of claim 10 wherein dehydrogenation conditions include a temperature of 1100° to 1300 ° F.

18. A process for dehydrocyclization of a feed containing $C_5$ to $C_{12}$ aliphatics in a multi reactor process comprising;

a. heating and vaporizing a liquid feed containing $C_5$ to $C_{12}$ aliphatics and having a pressure of at least 100 psig to produce a heated vapor stream having a pressure above 100 psig;

b. charging heated vapor to a first dehydrocyclization reactor operating at dehydrocyclization conditions including a pressure above 100 psig and containing a dehydrocyclization catalyst and converting a limited amount of said feed to produce a first reactor effluent containing produced hydrogen;

c. charging said first reactor effluent to at least one downstream dehydrocyclization reactor operating at less than ½ the absolute pressure of said first reactor and containing a dehydrocyclization catalyst and converting in said downstream reactor additional amounts of said feed; and d. removing from said at least one downstream reactor a reactor effluent stream comprising aromatic products and produced hydrogen as a product of the process.

19. The process of claim 18 wherein said first reactor operates at a pressure higher than 200 psig, said downstream reactor operates at a pressure lower than 100 psig, and said process operates with less than 0.5 moles of hydrogen added per mole of hydrocarbon added to said first reactor.

20. The process of claim 18 wherein pressure is reduced from said first reactor to said downstream reactor by disposing at least a portion of said catalyst in said first reactor as a fixed bed of catalyst in tubes having a length to diameter ratio of at least 20:1.

* * * * *